United States Patent [19]

Hoffman, Jr. et al.

[11] Patent Number: 5,197,977
[45] Date of Patent: Mar. 30, 1993

[54] DRUG DELIVERY COLLAGEN-IMPREGNATED SYNTHETIC VASCULAR GRAFT

[75] Inventors: Harmon Hoffman, Jr., Wyckoff, N.J.; Kemal Schankereli, Stillwater, Minn.; Milos Chvapil, Tucson, Ariz.

[73] Assignee: Meadox Medicals, Inc., Oakland, N.J.

[21] Appl. No.: 877,344

[22] Filed: Apr. 30, 1992

Related U.S. Application Data

[63] Continuation of Ser. No. 680,029, Mar. 28, 1991, abandoned, which is a continuation of Ser. No. 455,866, Dec. 21, 1989, abandoned, which is a continuation of Ser. No. 51,188, May 14, 1987, abandoned, which is a continuation of Ser. No. 575,091, Jan. 30, 1984, abandoned.

[51] Int. Cl.$^5$ .............................................. B61F 2/06
[52] U.S. Cl. ........................................ 623/1; 623/66; 427/2
[58] Field of Search ............. 623/1, 2, 11, 12, 66; 128/DIG. 8; 427/2

[56] References Cited

U.S. PATENT DOCUMENTS

| | | | |
|---|---|---|---|
| 3,272,204 | 9/1966 | Artandi | 623/1 |
| 3,425,418 | 2/1969 | Chvapil et al. | 623/1 |
| 3,928,653 | 12/1975 | Dowell, Sr. et al. | 426/657 |
| 4,047,252 | 9/1977 | Liebig et al. | 623/1 |
| 4,416,028 | 11/1983 | Eriksson et al. | 623/1 |
| 4,842,575 | 6/1989 | Hoffman, Jr. et al. | 623/1 |

FOREIGN PATENT DOCUMENTS

| | | | |
|---|---|---|---|
| 0000949 | 3/1979 | European Pat. Off. | 623/1 |
| 2601289 | 7/1977 | Fed. Rep. of Germany | 623/1 |
| 0904693 | 2/1982 | U.S.S.R. | 623/1 |

*Primary Examiner*—David Isabella
*Attorney, Agent, or Firm*—Blum Kaplan

[57] ABSTRACT

A collagen impregnated vascular graft including drug materials complexed with the collagen to be released slowly from the graft following implant. The graft is a porous synthetic vascular graft substrate having collagen fixed to the graft substrate and cross-linking the collagen in situ to render the porous substrate bloodtight. The drug materials complexed with the collagen fibrils may include antithrombic agents, antibacterial, antimicrobial agents, antifungal agents and the like.

16 Claims, 2 Drawing Sheets

DRUG DELIVERY COLLAGEN-IMPREGNATED SYNTHETIC VASCULAR GRAFT

This is a continuation of application Ser. No. 07/680,029 filed on Mar. 28, 1991, now abandoned, which is a continuation of application Ser. No. 07/455,866, filed on Dec. 21, 1989, now abandoned, which is a continuation of application Ser. No. 07/051,188, filed on May 14, 1987, now abandoned which is a continuation of application Ser. No. 06/575,091, filed on Jan. 30, 1984 for DRUG DELIVERY COLLAGEN-COATED SYNTHETIC VASCULAR GRAFT, and now abandoned.

BACKGROUND OF THE INVENTION

This invention relates to a synthetic vascular graft, and more particularly to a drug delivery blood-tight collagen-impregnated synthetic vascular graft which does not need to be pre-clotted and which acts as a reservoir for sustained release of a drug material after implant.

The replacement of segments of human blood vessels with synthetic vascular grafts is well accepted in the art. Synthetic vascular grafts have taken a wide variety of configurations and are formed of a wide variety of materials. Among the accepted and successful vascular graft implants are those which are formed from a biologically compatible material which retains an open lumen to permit blood to flow through the synthetic graft after implant. The grafts may be made from biologically compatible fibers, such as Dacron and Teflon, may be knitted or woven and may be of a mono-filiment yarn, multi-filiment yarn or staple yarn.

An important factor in the selection of a particular graft substrate is the porosity of the fabric wall of which the graft is formed. Porosity is significant because it controls the tendency to hemorrhage during and after implantation and controls the ingrowth of tissue into the wall of the graft. It is desirable that the vascular graft substrate be sufficiently blood-tight to prevent the loss of blood during implant, yet the structure must be sufficiently porous to permit ingrowth of fibroblast and smooth muscle cells in order to attach the graft to the host tissue. Synthetic vascular grafts of the type described in U.S. Pat. Nos. 3,805,301 and 4,047,252, assigned to the assignee of the subject application, are elongated flexible tubular bodies formed of a yarn such as Dacron. In the earlier patent, the graft is a warp knitted tube and in the latter issued patent it is a double-velour synthetic graft marketed under the trademark Microvel. These types of grafts have sufficiently porous structures to permit ingrowth of host tissue.

The general procedure for implantation includes the step of pre-clotting, wherein the graft is immersed in the blood of the patient an allowed to stand for a period of time sufficient for clotting to insue. After pre-clotting, hemorrhaging does not occur when the graft is implanted and growth of tissue is not impeded. Graft infection is a most serious complication and occurs in an average of two percent of prosthetic graft placements. It is associated with a high risk of limb loss and patient mortality is as high as 75% depending on the location of the graft. While infection usually becomes evident soon after surgery, the time may be extended which leads to more serious consequences.

An absorbable collagen reinforced graft is proposed in U.S. Pat. No. 3,272,204 wherein the collagen is obtained from the deep flexor tendon of cattle. Another reinforced vascular prosthesis is described in U.S. Pat. No. 3,479,670 which includes an open mesh cylindrical tube wrapped by an outer helical wrapping of fused polypropylene mono-filiment filled with collagen fibrils which are claimed to render the prosthesis impermeable to bacteria and fluids. The collagen fibrils utilized are the same as described in U.S. Pat. No. 3,272,204.

The synthetic vascular grafts suggested by the prior art are claimed to be suitable for many applications. However, it is desirable to provide a flexible vascular graft having zero porosity, one which is receptive to ingrowth of host tissue and serves as a reservoir for drug materials to be released slowly from the surface of the graft following implant.

SUMMARY OF THE INVENTION

A collagen impregnated synthetic vascular graft which provides a reservoir for the slow release of a drug material after implant is provided. The collagen fibrils in the graft are complexed with a drug material such as antibacterial agents, antithrombic agents and antiviral agents to insure against graft infection.

The porous graft substrate may be a tubular vascular graft formed of a Dacron material and may be woven or knit. The collagen source is an aqueous fibril dispersion of high purity including a plasticizer and is applied to the graft substrate by massage to cover at least the entire inner surface area to provide a flexible graft with good hand. After repeated application and drying, the collagen is cross-linked by exposure to formaldehyde vapor.

Accordingly, it is an object of the invention to provide an improved synthetic vascular graft.

Another object of the invention is to provide an improved collagen-impregnated synthetic vascular graft.

A further object of the invention is to provide an improved collagen-impregnated synthetic vascular graft wherein the collagen serves as a reservoir for the slow release of a drug after implantation.

Still another object of the invention is to provide an improved process for treating a synthetic vascular graft with collagen to render the graft blood-tight and serve as a reservoir for the slow release of a drug after implantation.

Still other objects and advantages of the invention will in part be obvious and will in part be apparent from the specification.

The invention accordingly comprises the article possessing the features, properties and the relation of elements and the several steps and the relation of one or more of such steps with respect to each of the others, which are exemplified in the following de&ailed disclosure, and the scope of the invention will be indicated in the claims.

BRIEF DESCRIPTION OF THE DRAWING

For a fuller understanding of the invention, reference is had to the following description taken in connection with the accompanying drawing, in which.

DESCRIPTION OF THE PREFERRED EMBODIMENTS

Figure 1:
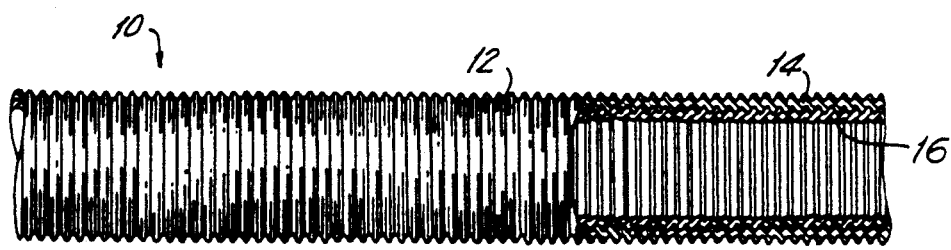
FIG. 1 is a partial cross-sectional view of a collagen-impregnated synthetic vascular graft in accordance with the invention.

A synthetic vascular graft 10 constructed and arranged in accordance with the invention is shown in FIG. 1. Graft 10 includes a tubular substrate portion 12 which is formed of a biologically compatible filamentary synthetic material, preferably a polyethylene terephthalate, such as Dacron. Substrate 12 is a porous Dacron warp knit fabric having an inner and outer velour surface of the type described in U.S. Pat. No. 4,047,252. While tubular portion 12 is formed of Dacron, any biocompatible filimentary material may be used for the substrate provided it may be fabricated into a porous structure which will permit tissue ingrowth and maintain an open lumen for flow of blood.

Figure 2:
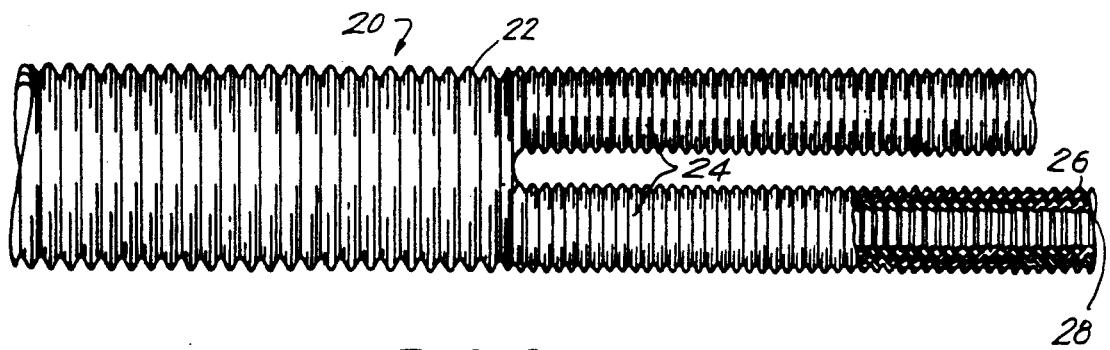
FIG. 2 is a partial cross-sectional view of a branched tubular graft of the type illustrated in FIG. 1.

The inner surface of tubular portion 12 has a collagen coating shown as 16. Collagen coating 16 is formed from a series of at least three layers of applied collagen fibrils. FIG. 2 shows a bifurcated collagen-coated graft 20. Graft 20 includes a main tubular portion 22 and two branches 24. Main tubular portion 22 and bifurcated portions 24 are formed from a Dacron knit substrate 26. The inner surface coating of substrate 26 is collagen coating 28 also formed of at least three layers of collagen fibrils.

Porous vascular graft substrates suitable for use in accordance with the invention, preferably are produced from Dacron multi-filiment yarns by knitting or weaving processes which are commonly used in manufacture of these products. Generally, the porosity of the Dacron substrate ranges from about 2,000 to 3,000 ml/min-$cm^2$ (purified water at 120 mm Hg). The cross-linked collagen is applied by filling a tubular substrate with a slurry of collagen fibrils and plasticizer and massaging manually, removing the excess and permitting the deposited dispersion to dry. After the final application, the collagen is cross-linked by exposure to formaldehyde vapor, air dried and then vacuum dried to remove excess moisture and excess formaldehyde. The collagen impregnated grafts in accordance with the invention have essentially zero porosity.

The following examples are set forth to illustrate the method of preparing purified collagen from bovine skin and coated grafts in accordance with the invention. The examples are set forth for purposes of illustration and not intended in a limiting sense.

EXAMPLE 1

Fresh calf skins were mechanically stripped from young calves, fetuses or stillborns and washed in a rotating vessel with cold running water until the water was observed to be free from surface dirt, blood and/or tissues. The subcutis was mechanically cleaned to remove contaminating tissues, such as fat and blood vessels. Subsequently, the skins were cut in the longitudinal direction into strips about 12 cm wide and were placed in a wood or plastic vessel as commonly used in the leather industry.

The skins were dehaired by using a flusher solution of 1M $Ca(OH)_2$ for 25 hours. Alternatively, the skin may be dehaired by mechanical means or by a combination of chemical and mechanical means. Following the dehairing, the skins were cut into small size pieces about 1"×1" and were washed in cold water.

Following washing, 120 Kg of the bovine skin was placed in a vessel having 260 L water, 2 L NaOH (50%) and 0.4 L $H_2O_2$ (35%). The components were mixed slowly for 12 to 15 hours at 4° C. and washed with an excess of tap water for 30 minutes to provide partially purified skins. The partially purified skins were treated in a solution of 260 L water, 1.2 L NaOH (50%) and 1.4 Kg CaO for 5 minutes with slow mixing. This treatment was continued twice daily for 25 days. Following this treatment, the solution was decanted and discarded and the skins were washed with an excess of tap water for 90 minutes under constant stirring.

The skins were acidified by treatment with 14 kg HCl (35%) and 70 L water while subjecting the skins to vigorous stirring. The acid was allowed to penetrate the skins for about 6 hours. Following acidification, the skins were washed in an excess of tap water for about 4 hours or until a pH of 5.0 was reached. The pH of the skins was readjusted to 3.3–3.4 using acetic acid with a 0.5% preservative. The purified skin was then passed through a meat grinder and extruded under pressure through a series of filter sieves of constantly decreasing mesh size. The final product was a white homogeneous smooth paste of pure bovine skin-derived collagen.

In order to impart adequate pliability to the grafts in the dry state, plasticizers are added to the collagen slurry before application. Suitable plasticizers include glycerine, sorbitol or other biologically acceptable plasticizers. In a collagen slurry containing between about 0.5 to 5.0 percent collagen by weight, the plasticizer is present in an amount between about 4 and 12 weight percent.

Among the most important properties obtained when treating a synthetic vascular graft with collagen fibrils in accordance with the invention is reduction of porosity of the porous substrate to about zero. The porosity of twenty randomly selected uncoated Microvel Dacron synthetic vascular grafts have a mean porosity to purified water of 1796 ml/min-$cm^2$ at 120 mm Hg with a standard deviation of 130. After applying several collagen treatments, the porosity is reduced to zero. The following example illustrates the method of treating the graft substrate.

EXAMPLE 2

A 50 cc syringe is filled with an aqueous slurry of 2% purified bovine skin collagen prepared in accordance with Example 1. The collagen slurry includes 8% glycerol, 17% ethanol and the remainder water and a viscosity of 30,000 cps. The syringe is placed into one end of a Meadox Medical Microvel Dacron graft 8 mm in diameter by approximately 12 cm in length. The slurry is injected into the lumen of the Microvel graft and it is massaged manually in order to cover the entire inner surface area with the collagen slurry. Any excess collagen slurry is removed through one of the open ends. The graft is permitted to dry for about ½ hour at room temperature. The applying and drying steps were repeated three more times.

Following the fourth application, the collagen was cross-linked by exposure to formaldehyde vapor for 5 minutes. The cross-linked graft was then air dried for 15 minutes and then vacuum dried for 24 hours to remove moisture and any excess formaldehyde.

EXAMPLE 3

The blood-tightness of a collagen-impregnated vascular graft prepared in accordance with Example 2 was tested as follows. A Microvel graft 8 mm × 12 cm was attached to a blood reservoir at a pressure of 120 mm Hg due to the height of the reservoir. Heprin stabilized blood was passed through the graft and blood collected through the grafts was determined and expressed in ml per min-cm$^2$. The porosity over 5 runs was determined to be 0.04, 0.0, 0.0, 0.04 and 0.03. This represents a mean porosity of 0.022 ml/min-cm$^2$ which was considered zero, as the value is within the experimental error of the study.

In order to compare this result with the blood loss for untreated Microvel graft, the experiment was repeated using an untreated graft. The mean porosity was 36 ml/min-cm$^2$.

The antimicrobial activity of a collagen fabric graft prepared in accordance with the invention is demonstrated as follows.

EXAMPLE 4

The porosity of a collagen impregnated fabric graft is reduced to less than about 1 percent of an uncoated graft after three applications of collagen. A standard water porosity test used to measure water porosity of a graft is as follows. A column of water equivalent to 120 mm Hg pressure is allowed to flow through a one-half cm$^2$ orifice having a sample of graft over the orifice for one minute. The amount of water collected was measured. The milliliters of water collected per minute per cm$^2$ squared area was calculated. Several readings are taken for each sample. The porosity is reported as follows:

porosity = ml/min/cm$^2$

The water porosity of a Microvel graft fabric was about 1,900 ml/min/cm$^2$. The porosity after treating was as follows:

| Number of Applications | Porosity |
|---|---|
| 0 | 1,900 |
| 1 | 266 |
| 2 | 146 |
| 3 | 14 |
| 4 | 5 |
| 5 | 2.2 |
| 6 | 0 |

In each case the collagen was a bovine skin derived-plasticized slurry prepared in accordance with the composition described in Example 2. Based on these results, it is preferable to apply collagen in at least three or four applications of fibrils, and most preferably four or five with drying between each application and cross-linking to fix the collagen to the substrate.

In accordance with the invention, the collagen in at least the last two application to a porous substrate are chemically modified to incorporate a drug or an antithrombic agent, such as heprin, in order to prevent infection and to inhibit clotting along the inner surface of the prosthesis. As noted, the collagen may be complexed with a variety of drugs, such as antibacterial agents, antimicrobial agents or antifungal agents in order to prevent graft infection. Typical antibacterial agents which may be utilized include oxacillin, gentamicin, tetracycline, cephalosporin and the like which may be complexed with the collagen fibrils prior to application to the graft substrate.

In addition to reduced porosity, collagen impregnated vascular grafts in accordance with the invention exhibit reduced thrombogenicity compared to untreated grafts.

EXAMPLE 5

A homogeneous slurry of bovine skin derived collagen prepared in accordance with Example 1 was prepared containing 1% bovine skin derived collagen, 8% glycerol, .17% ethanol with the remainder water. Ceclor, a cephalosporin antibiotic of Eli Lilly and Company which inhibits the growth of *Staphylococus aureus* and *Escherichia coli*, was blended into the slurry at a concentration of 20 mg per ml. The collagen slurry including the Ceclor was massaged into a double velour Dacron fabric on both sides with ½ hour drying periods between applications. The treatment resulted in the addition of 3.1 mg collagen per cm$^2$.

As a control, Dacron double velour fabric was also impregnated with the same collagen slurry omitting the Ceclor antibiotic. This control had an addition of 4.1 mg of collagen per cm$^2$.

Both pieces of treated fabric were immersed for 1 minute in 4% formaldehyde, 10% glycerol solution, vacuum desiccated for 64 hours and sterilized using gamma radiation.

The antimicrobial activity of the collagen impregnated Dacron vascular graft fabric, impregnated with Ceclor, was determined in an agar diffusion assay. Fabric swatches of 1 cm$^2$ were placed on innoculated agar surfaces resulting in growth inhibition zones which indicated that the antibiotic was active against *S. aureus* (34 mm zone of inhibition) and *E. coli* (29 mm zone of inhibition). The untreated control collagen impregnated vascular graft fabric did not exhibit any anitimicrobial effect. The results are tabulated in the following Tables I and II.

TABLE I

| TREATED COLLAGEN IMPREGNATED FABRIC | | | | |
|---|---|---|---|---|
| | PLATE 1 | PLATE 2 | PLATE 3 | x$_3$ |
| S. aureus | 36 mm | 31 mm | 35 mm | 34 mm |
| E. coli | 33 mm | 28 mm | 27 mm | 29 mm |

TABLE II

| UNTREATED COLLAGEN IMPREGNATED FABRIC | | | | |
|---|---|---|---|---|
| | PLATE 1 | PLATE 2 | PLATE 3 | x$_3$ |
| S. aureus | 0 | 0 | 0 | 0 |
| E. coli | 0 | 0 | 0 | 0 |

EXAMPLE 6

A collagen slurry prepared in accordance with Example 1 containing 13.2% collagen protein (determined by its hydroxyproline content) was mixed in a 1:3 ratio with water (W) to form a 3.3 weight percent homogeneous collagen gel (G). The pH of the collagen gel was adjusted to 3.8 and 20 mg of tetracycline (TC) was added per millimeter of gel. Immediately before injection into two rabbits, the collagen gel-tetracycline complex was mixed with glutaraldehyde (0.3 ml of 3% glutaraldehyde per ml of the gel) and injected through 18 gage needles into the subcutis. Two rabbits as controls were injected with a similar dose of tetracycline and water, 20 mg TC/ml water/kg body weight.

In order to study the rate of tetracycline released from the injected site, blood was collected at various time intervals from the rabbit's ear vein. The content of TC in the blood was measured according to the procedure of Wilson, et al. (Clin. Chem. Acta., 36; 260, 1972). The results of the TC analysis in the blood of the total of four rabbits collected within 2 hours to 7 days postinjection are set forth in FIG. 3.

Figure 3:
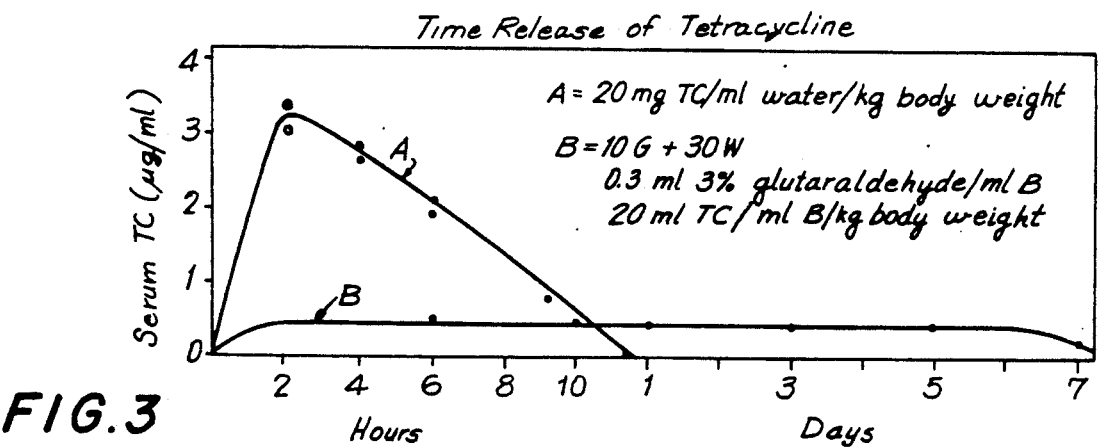
FIG. 3 is a graph illustrating sustained release of tetracycline from a collagen slurry in rabbits.

FIG. 3 shows that after injection of TC in water the drug reaches its maximum in the serum within two hours as shown by Curve A. At 11 hours the TC is no longer detectable. When tetracycline was administered in a collagen gel cross-linked with glutaraldehyde (10G+30W), the level of serum TC remained stable for about 6 days as shown by Curve B. Thus, administration of TC in collagen gel prolonged the effective release of the drug 25 times compared with injection in an aqueous medium only.

EXAMPLE 7

Figure 4:
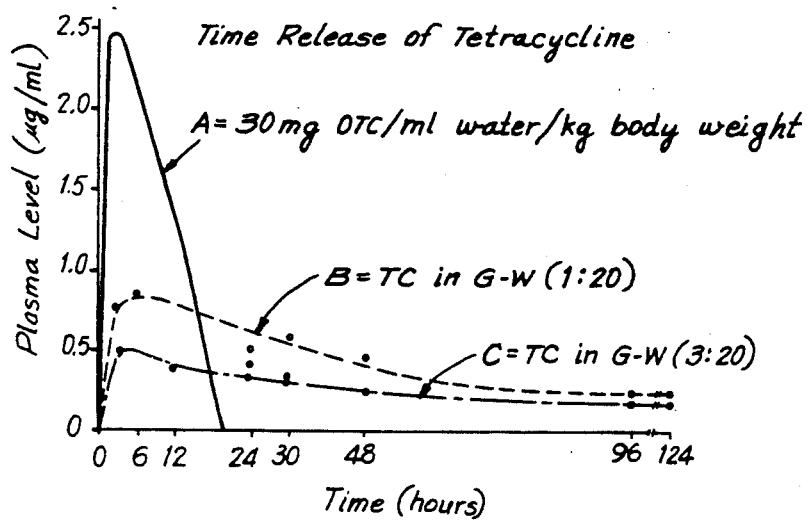
FIG. 4 is a graph illustrating sustained release of tetracycline at different collagen gel concentrations.

The test described in Example 5 was repeated using collagen gel at two different concentrations for the final injection. Additionally, the tetracycline content was 30 mg oxytetracycline (OTC)/ml gel/kg body weight at a dose of 1 ml/kg of body weight, or 50% more tetracycline per dose than Example 5. The results illustrated in FIG. 4 show that the concentration of collagen in the gel affects the rate of OTC release from the collagen matrix. The denser the collagen gel, the slower is the release of the drug. In this Example, the kinetics of the OTC release was studied for a total of 124 hours after injection of the tested complex in the subcutis of a total of six rabbits.

In FIG. 4 Curve A shows that the OTC in water reaches its maximum in the serum shortly after injection and is not detectable after 18 or 20 hours. Curve B shows OTC serum concentration for OTC complexed with a collagen matrix at a weight ratio of gel complex to water of 1:20 and Curve C at 3:20. Release of the OTC is more rapid for the less concentrated gel of Curve B.

EXAMPLE 8

Collagen gel containing 3% collagen, measured as a dry substance, was mixed with tetracycline to form two concentrations, containing (A) 50 mg TC/ml and (B) 100 mg TC/ml gel. After mixing with 0.3 ml of 3% glutaraldehyde (Gl) per ml gel (G), complex A was injected at a dosage of 2 ml/kg body weight and complex B was injected at a dosage of 1 ml/kg. Plasma level concentrations of TC in mg/ml are shown in Curves A and B of FIG. 5. Complex A was also injected at a dosage of 1 ml/kg and is shown by Curve C in FIG. 5. The actual plasma levels of tetracycline during the period up to 5 days postinjection are shown in FIG. 5.

Figure 5:
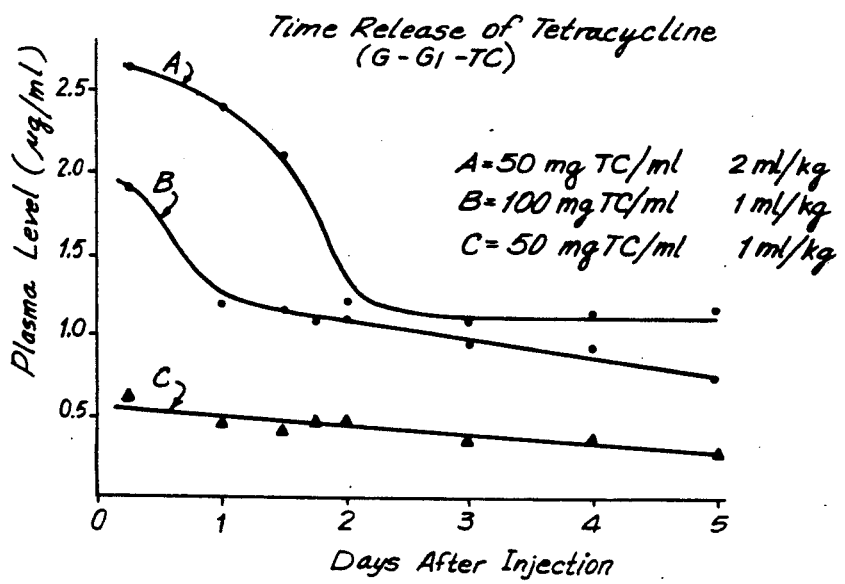
FIG. 5 is a graph illustrating sustained release of tetracycline in a collagen gel at different concentrations and dosage.

The data of FIG. 5 show that both the actual concentration of tetracycline as well as the surface geometry of the implant affects the level of magnitude of drug release from the gel and the level of tetracycline in the plasma.

It will thus be seen that the objects set forth above, among those made apparent from the preceding description, are efficiently attained and, since certain changes may be made in the article and in carrying out the above process set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Particularly it is to be understood that in said claims, ingredients or compounds recited in the singular are intended to include compatible mixtures of such ingredients wherever the sense permits.

What is claimed is:

1. A synthetic vascular graft comprising:
   a tubular flexible porous graft substrate of a synthetic fiber having a porosity of less than about 3,000 ml/min cm$^2$ (purified water at 120 mm Hg);
   the graft substrate having on the inner surface and extending through the porous substrate to the outer surface cross-linked water insoluble collagen fibrils complexed with an effective amount of a drug and admixed with a plasticizer for rendering the graft blood-tight and flexible and providing for substained release of the drug portion of the complex after immplantation,
   the collagen fibrils applied by application of an aqueous slurry of water-insoluble collagen fibrils which has been massaged through the substrate and dried and cross-linked.

2. The vascular graft of claim 1, wherein the drug portion of the complex is a pharmaceutical agent selected from the group consisting of antimicrobial agents, antibacterial agents, antifungal agents, antithrombogenic agents, cell-proliferation promoting agents and mixtures thereof.

3. The vascular graft of claim 1, wherein the collagen fibril-drug complex is applied in at least three applications formed by applying aqueous slurries of collagen fibrils which have been dried between applications and cross-linked after application.

4. The vascular graft of claim 1, wherein the porous substrate is polyethylene terephthalate.

5. The vascular graft of claim 4, wherein the porous substrate is knitted.

6. The vascular graft of claim 4, wherein the porous substrate is woven.

7. The vascular graft of claim 4, wherein the inner and outer surface of the substrate have a velour surface.

8. The vascular graft of claim 1, wherein the collagen fibrils-drug complex is cross-linked by exposure to formaldehyde vapor.

9. The vascular graft of claim 1, wherein the plasticizer is a biologically compatible polyhydric material.

10. The vascular graft of claim 9, wherein the plasticizer is sorbitol.

11. The vascular graft of claim 9, wherein the plasticizer is glycerine.

12. A synthetic vascular graft comprising:
    a tubular flexible porous polyethylene terephthalate graft substrate having a porosity of less than about 3,000 ml/min-cm$^2$ (purified water at 120 mm Hg);
    the inner surface having been treated with collagen fibrils complexed with a drug and admixed with a plasticizer which extends into the porous structure of the substrate and covers the outer surface;
    the collagen applied by depositing an aqueous slurry containing between about 0.5 to 5.0 weight percent water-insoluble collagen fibrils and between about 4 to 12 weight percent plasticizer to the lumen of the substrate and massaged through the substrate and dried and cross-linked.

13. The synthetic vascular graft of claim 12, wherein the collagen is applied in at least three applications.

14. The synthetic vascular graft of claim 13, wherein the aqueous slurry contains between about 1.5 to 4.0 total weight percent collagen fibrils.

15. The synthetic vascular graft of claim 14, wherein the slurry contains between about 6 to 10 weight percent plasticizer.

16. The synthetic vascular graft of claim 15, wherein the collagen has been cross-linked with formaldehyde.

* * * * *